(12) United States Patent  (10) Patent No.: US 7,708,110 B2
Leong et al.  (45) Date of Patent: May 4, 2010

(54) BANDLESS HEARING PROTECTOR AND METHOD

(75) Inventors: Waihong Leong, Roswell, GA (US);
Steven Craig Gehling, Cumming, GA (US); Scott M. Belliveau, Plainfield, IL (US); Sean S. Corbin, Morton Grove, IL (US); Keith Grider, Chicago, IL (US); Anne Clare Moser, Chicago, IL (US); Aleksey Pirkhalo, Chicago, IL (US); Abby Elizabeth Sturges, Chicago, IL (US); James Wolford, Chicago, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 26 days.

(21) Appl. No.: 11/821,391

(22) Filed: Jun. 22, 2007

(65) Prior Publication Data
US 2008/0264715 A1 Oct. 30, 2008

Related U.S. Application Data

(63) Continuation-in-part of application No. 11/799,264, filed on Apr. 30, 2007.

(51) Int. Cl.
*H04R 25/02* (2006.01)
*A61F 11/08* (2006.01)
*A61F 11/12* (2006.01)
*H04R 25/00* (2006.01)
*A61F 11/06* (2006.01)

(52) U.S. Cl. .......... 181/135; 181/130; 381/328; 381/330; 381/380; 381/374; 128/867

(58) Field of Classification Search ............ 181/135, 181/130, 129, 131; 381/328, 329, 330, 72, 381/23.1, 381, 374, 380; 128/864, 867
See application file for complete search history.

(56) References Cited

U.S. PATENT DOCUMENTS 466,725 A 1/1892 Miltimore (Continued)

FOREIGN PATENT DOCUMENTS

FR 2 157 177 A5 6/1973

(Continued)

OTHER PUBLICATIONS

American Society for Testing Materials (ASTM) Designation: D 570-98 (Reapproved 2005), "Standard Test Method for Water Absorption of Plastics," pp. 1-4, published Jan. 2006.

(Continued)

*Primary Examiner*—Edgardo San Martin
(74) *Attorney, Agent, or Firm*—Denise Stoker; Nathan P. Hendon

(57) ABSTRACT

A hearing protection device and method for a human ear. A plug member caps or enters ear canal, and may be shaped to conform to the external auditory meatus. The device is biased at least in part by a pressure pad to provide some force against the plug member. An optional handle may be provided to assist with temporarily pulling the plug member away from the ear canal or providing adjustment. An optional bow member clips about the pinna. The device may be adapted for use as an ear phone.

19 Claims, 10 Drawing Sheets

U.S. PATENT DOCUMENTS

| | | | |
|---|---|---|---|
| 1,576,938 A * | 3/1926 | Struxiano | 381/380 |
| 1,668,890 A * | 5/1928 | Curran et al. | 181/130 |
| 2,487,038 A * | 11/1949 | Baum | 181/135 |
| 2,939,923 A * | 6/1960 | Henderson | 381/330 |
| 3,667,569 A | 6/1972 | Mackey et al. | |
| 3,682,268 A | 8/1972 | Gorike | |
| 3,783,201 A * | 1/1974 | Weiss et al. | 381/324 |
| 3,915,166 A | 10/1975 | McCrink | |
| RE29,487 E | 12/1977 | Gardner, Jr. | |
| 4,223,189 A | 9/1980 | Warren | |
| 4,490,857 A | 1/1985 | Leight et al. | |
| 5,420,381 A | 5/1995 | Gardner, Jr. et al. | |
| 5,450,496 A | 9/1995 | Burris et al. | |
| 5,824,966 A | 10/1998 | Leight | |
| 6,038,329 A * | 3/2000 | Lee | 381/370 |
| 6,105,714 A | 8/2000 | Lindgren | |
| 6,728,388 B1 | 4/2004 | Nageno et al. | |
| 6,751,331 B2 | 6/2004 | Eisenbraun | |
| 6,785,396 B2 | 8/2004 | Shirata | |
| 6,804,364 B1 | 10/2004 | De Jonge | |
| 6,810,987 B1 * | 11/2004 | DeKalb | 181/129 |
| 6,819,772 B2 | 11/2004 | Amae | |
| 2002/0172386 A1 * | 11/2002 | Bayer | 381/330 |
| 2003/0044038 A1 | 3/2003 | Shirata | |
| 2003/0112992 A1 * | 6/2003 | Rapps | 381/381 |
| 2004/0170294 A1 | 9/2004 | Murozaki et al. | |
| 2005/0002539 A1 * | 1/2005 | Nielsen | 381/312 |
| 2006/0198544 A1 | 9/2006 | Yueh | |
| 2006/0215864 A1 * | 9/2006 | Espersen et al. | 381/330 |
| 2008/0037817 A1 * | 2/2008 | Ewert et al. | 381/380 |
| 2008/0137897 A1 * | 6/2008 | Liu | 381/380 |
| 2008/0144877 A1 * | 6/2008 | Ham et al. | 381/379 |

FOREIGN PATENT DOCUMENTS

| | | |
|---|---|---|
| FR | 2 558 055 A1 | 7/1985 |
| GB | 191504579 A | 2/1916 |
| GB | 0 258 280 A | 2/1927 |
| GB | 0 833 506 A | 4/1960 |
| GB | 2 374 684 A | 10/2002 |
| GB | 2 375 967 A | 12/2002 |
| GB | 2 407 513 A | 5/2005 |

OTHER PUBLICATIONS

American Society for Testing Materials (ASTM) Designation: D2240-05, "Standard Test Method for Rubber Property—Durometer Hardness," pp. 1-13, published Sep. 2005.

American Society for Testing Materials (ASTM) Designation: D2856-94, "Standard Test Method for Open-Cell Content of Rigid Cellular Plastics by the Air Pycnometer," pp. 143-148, published May 1994.

American Society for Testing Materials (ASTM) Designation: D3574-05, "Standard Test Methods for Flexible Cellular Materials—Slab, Bonded, and Molded Urethane Foams," pp. 1-25, published Aug. 2005.

"Koss Titanium Earclips with Volume Control," sold by RadioShack® on Internet web page "http://www.radioshack.com/sm-koss-titanium-earclips-with-volume-control-pi-2206192.html" viewed and printed Apr. 6, 2007, pp. 1-2.

"Quiet Pro®," Internet web page "http://www.nacre.no/", Nacre®, Trondheim, Norway, viewed and printed Jun. 21, 2007, 1 page.

American National Standard, ANSI S3.19-1974 (R 1979) (ASA 1-1975), "Method for the Measurement of Real-Ear Protection of Hearing Protectors and Physical Attenuation of Ear Muffs," published by the Acoustical Society of America, pp. 1-9.

* cited by examiner

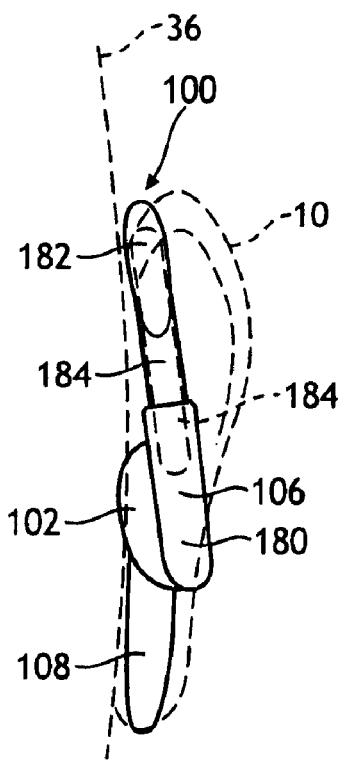
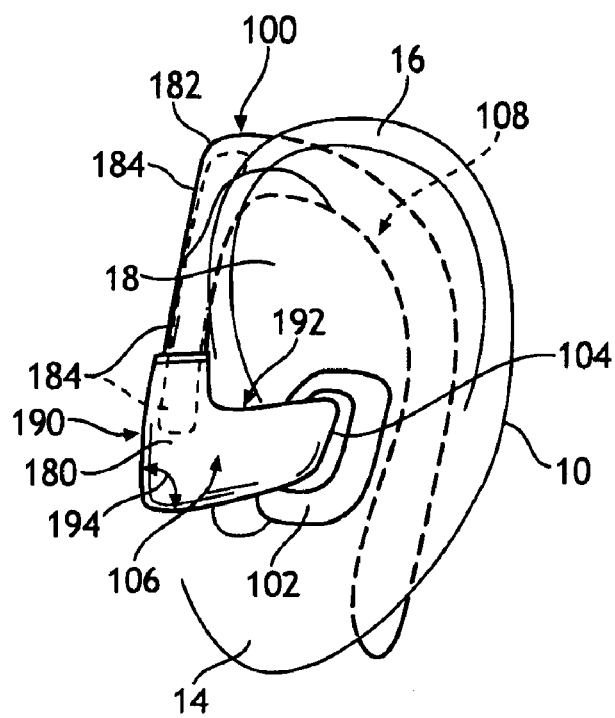
FIG. 9          FIG. 10
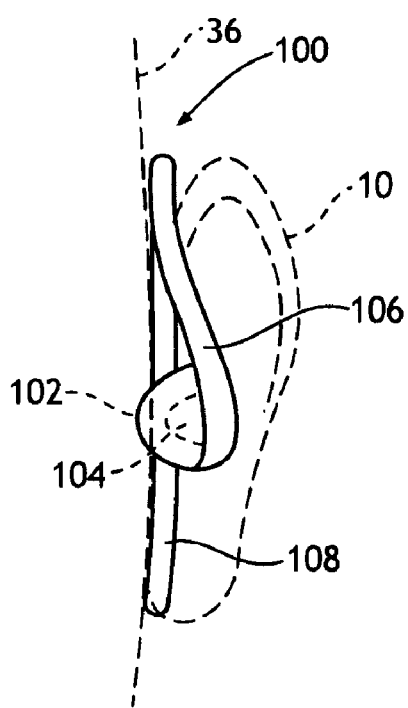
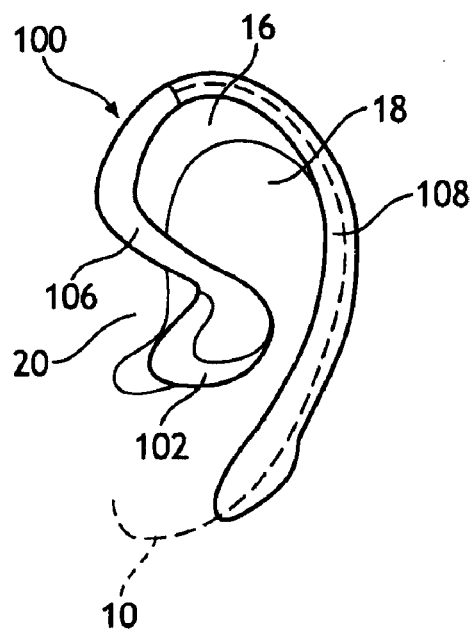
FIG. 11         FIG. 12

BANDLESS HEARING PROTECTOR AND METHOD

This application is a continuation-in-part of application Ser. No. 11/799,264 filed on Apr. 30, 2007.

BACKGROUND OF THE INVENTION

High level sound vibrations and perhaps particularly the steady recurring sounds or din in industrial operations are known to cause traumatic hearing impairments and even loss of hearing. Often these types of impairments do not respond to hearing aids or surgery. As would be expected, there are numerous types of hearing protectors for noise deadening or noise reduction.

One type of conventional hearing protection device are foam ear plugs that may be compressed and inserted into the ear, and then allowed to expand to fit the ear canal. While these types of ear plugs may be useful, they can be uncomfortable and difficult to insert correctly. Furthermore, handling ear plugs to compress, remove or replace may be unsanitary.

Another type of conventional hearing protection device includes a U-shaped headband having an inwardly directed ear plug affixed to each of the opposed ends. While it is easy and more sanitary to temporarily pull an ear plug away from the ear, the conventional headband may have certain drawbacks and deficiencies.

For some persons, ear bands can cause pressure and are uncomfortable to wear for long periods of time. The headband can be shaped such that portions of the headband may be close to or touching the wearer's head, and can become irritating and uncomfortable to the wearer. In addition, there is no mechanism for adjusting the headband to allow for varying head sizes. A wearer with a large head requires a large distance between the headband ends on which the ear plugs are attached. Unfortunately, as the distance between the headband end increases, so does the tension in the headband. Accordingly, wearers with relatively large heads may experience discomfort due to this high tension in the headband.

In light of the foregoing problems and issues discussed above, it is desirable to have a hearing protection device that can comfortably fit a wide variety of users. It is also desirable to have a hearing protection device that may be temporarily moved away from the ear without contamination by the hand.

SUMMARY OF THE INVENTION

In one aspect of the present invention, there is provided a bandless hearing protection method including the steps of covering the ear canal with a compliant plug member adapted to be disposed against the ear canal, and exerting force against the plug member using a pressure member that is adapted to be seated against external auditory meatus.

Other features of the invention will be in part apparent and in part pointed out hereinafter as well as better understood by practice of the invention. It is to be understood that both the foregoing general description and the following detailed description are exemplary and are intended to provide further explanation of the invention claimed. The accompanying drawings, which are incorporated in and constitute part of this specification, are included to illustrate and provide a further understanding of the bandless hearing protection device that is the present invention.

BRIEF DESCRIPTION OF THE DRAWINGS

A full an enabling disclosure of the present invention, including the best mode thereof, directed to one of ordinary skill in the art, is set forth more particularly in the remainder of the specification, which makes reference to the appended figures in which:

FIG. 9 is a front elevation view of a fifth embodiment of the hearing protector of the present invention, shown in a biased state as it engages an ear.

FIG. 10 is a side elevation view of the hearing protector of FIG. 9.

FIG. 11 is a front elevation view of a fifth embodiment of the hearing protector of the present invention, shown in a biased state as it engages an ear.

FIG. 12 is a side elevation view of the hearing protector of FIG. 11.

DETAILED DESCRIPTION OF THE PRESENT INVENTION

Figure 1:
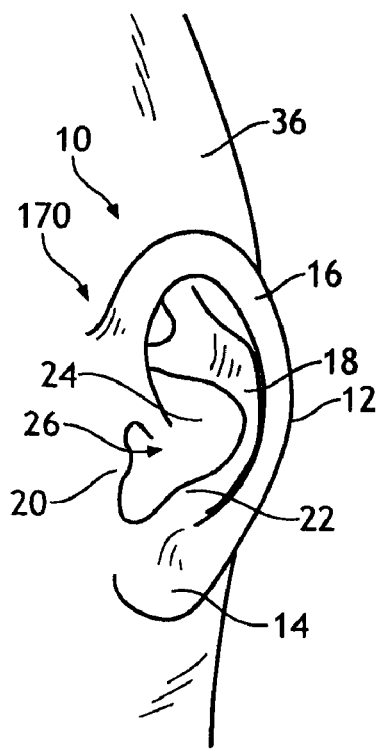
FIG. 1 is a side view of a human ear, illustrated to provide context for the present invention.
Figure 2:
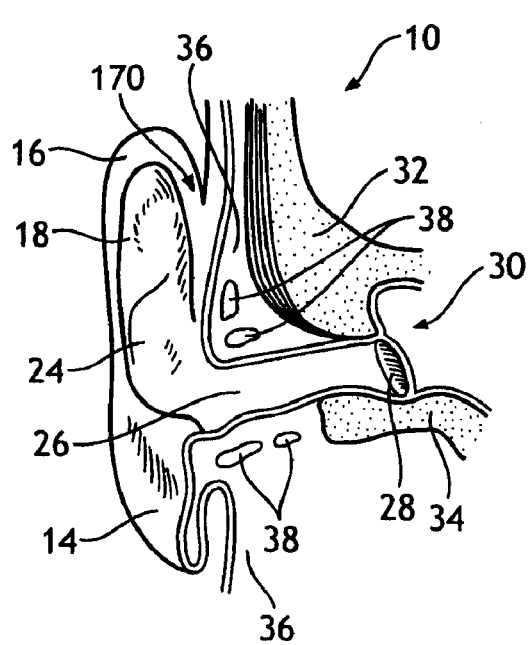
FIG. 2 is a front partial cross-section of a human ear, illustrated to provide context for the present invention.

The present invention is a hearing protector for the human ear 10. In order to provide context for the present invention, a brief discussion of human ear anatomy is presented. Referring to FIG. 1, the externally visible anatomy of the human ear 10 is largely defined by the pinna 12. The pinna 12 has various contours and folds which aid hearing, such as the lobe 14, helix 16, anti-helix 18, tragus 20, and anti-tragus 22. The concha 24 is an indented region roughly defined by the anti-helix 18, tragus 20, and anti-tragus 22. In the concha 24 region, one will find the opening to the ear canal 26. Referring now to FIG. 2, the interior of the ear is shown. In particular, the ear canal 26 is an elongated channel that terminates at the ear drum 28. Beyond the ear drum 28 is a region known as the middle ear 30. The ear drum 28 and the section of ear canal 26 in closest proximity thereto is located between two bony parts of skull, namely the temporal bone 32 and the occipital bone 34. Such bony parts, along with the entire skull, are covered by flesh and adipose material, generically referred to as tissue 36. The pinna 12 is connected to the tissue 36. The pinna 12 stiffness and shape is defined by cartilage 38, seen in cross-section in FIG. 2.

The present invention is a hearing protector 100 that clips to the pinna 12. The hearing protector may be unitary in construction, or assembled from two or more separate parts. Further, the hearing protector 100 will have a left or right orientation, depending on whether it is adaptable for the left or right ear. Regardless of the number of parts or the orientation of hearing protector 100, each embodiment of the present invention has several general sections. For instance, as seen in the embodiment shown in FIGS. 6-7, there is a plug 102 connected to a neck 104. Plug 102 is a pliable member that may conform to a portion of the ear canal 26, or at least the entrance of the ear canal at concha 24. An "ear clip" is defined by a neck 104 that extends from a shoulder 106, and which is connected to an arm 108. Together, the shoulder 106 and arm 108 form a "bow member" that generally extends from the tragus 20, upward to where helix 16 meets tissue 36, and down around the pinna 12 adjacent to where concha 24 meets tissue 36. The arm 108 may further wrap around and contact the lobe 14. The bow member may be biased such that when the hearing protector is clipped to the pinna 12, pressure is applied to the neck 104, forcing the plug 102 toward ear canal 26. Thus, the neck 104 is a "pressure member." Details of the various embodiments of the present invention are described below.

Figure 3:
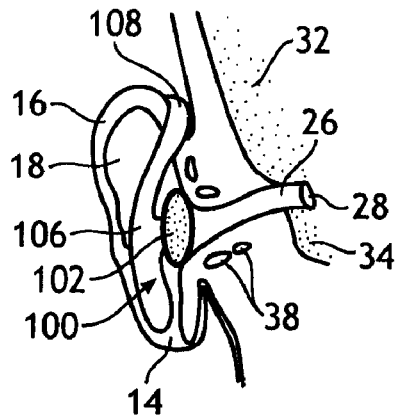
FIG. 3 is the human ear as shown in FIG. 2, with one embodiment of the hearing protector of the present invention disposed on the ear, showing a plug member that covers the ear canal entrance.
Figure 4:
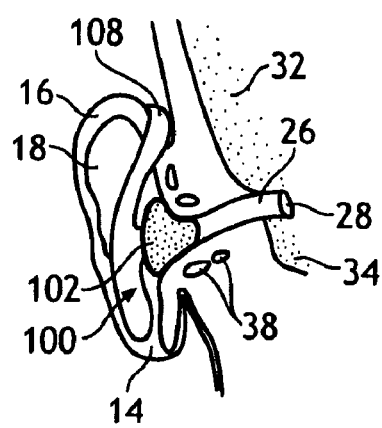
FIG. 4 is the human ear as shown in FIG. 2, with a second embodiment of the hearing protector of the present invention disposed on the ear, showing a plug member that partially enters the ear canal.
Figure 5:
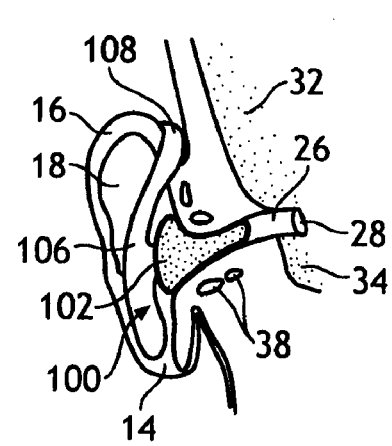
FIG. 5 is the human ear as shown in FIG. 2, with a third embodiment of the hearing protector of the present invention disposed on the ear, showing a plug member that fully enters the ear canal.

Hearing protectors 100 fall generally into three categories, including protectors that covers the entrance to ear canal 26 (referred to as cap devices) (FIG. 3.), protectors which partially enter and seal ear canal 26 between the sections of ear cartilage 38 (referred to as semi-insert devices) (FIG. 4.), and protectors that enter the ear canal and extend further toward the ear drum even with or just past the ear cartilage 38 (referred to as full-insert devices) (FIG. 5).

Hearing protectors 100 which enter the ear canal to a greater degree offer better protection against harmful noise levels because vibrations from the ear cartilage and ear canal tissue is attenuated, and the ear canal is at least partially sealed against the noisy environment. However, full-insert and even semi-insert devices may be less comfortable than those which simply cap the ear canal 26. Typically, plugs 102 that cap the ear canal 26 are used for intermittent noise exposures where lighter weight and improved low frequency attenuation are desirable. As used herein, "hearing protectors" refers generally to hearing protectors falling into one of the three categories described above. For reasons of simplicity, the embodiments of the present invention illustrated in FIGS. 6-25 include plugs 102 that operate as cap devices. However, it should be understood that the plugs 102 could be enlarged such that they operate as semi-insert or full-insert devices as shown in FIGS. 4 and 5, respectively.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Figure 6:
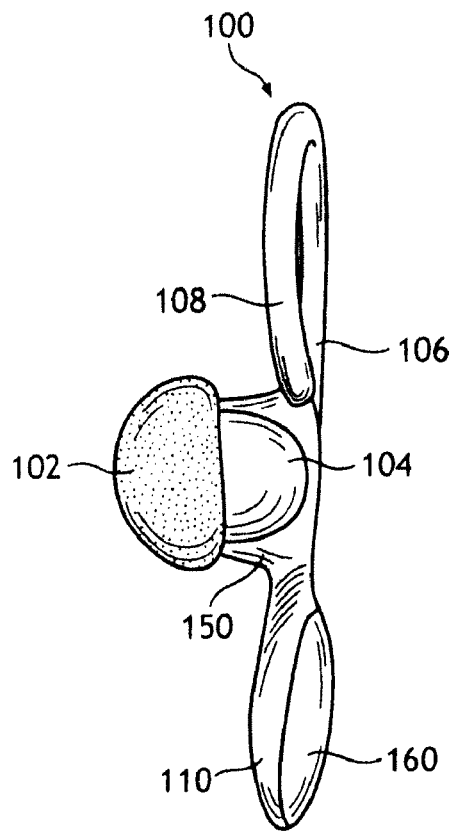
FIG. 6 is a front elevation view of a fourth embodiment of the hearing protector of the present invention, shown in a biased state.
Figure 7:
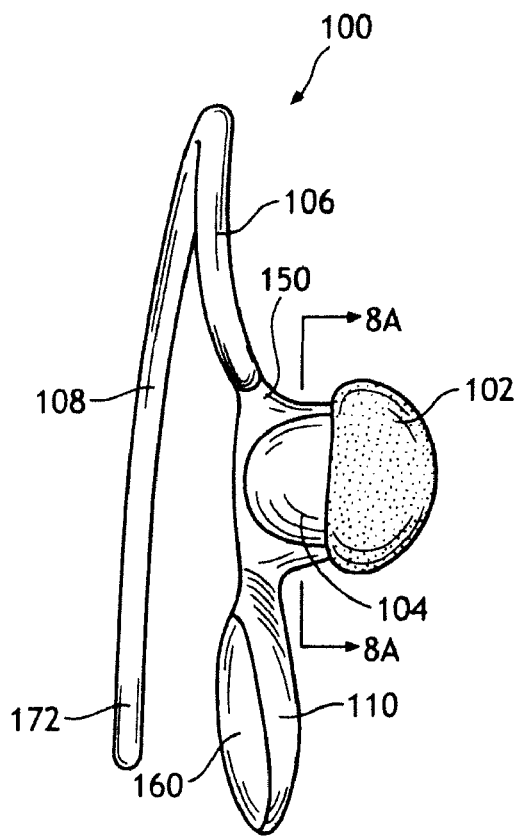
FIG. 7 is a front elevation view of the hearing protector of FIG. 6, shown in an unbiased state.

As shown in FIGS. 6-7, a first embodiment of hearing protector 100 desirably has a unitary construction, with the possible exception of the plug 102. The neck 104, shoulder 106, handle 110, and arm 108 may be molded from a plastic material having the following characteristics: flexible enough to move the arm 108 to the backside of pinna 12 as neck 104 is positioned near the ear canal 26; durable enough to be used more than one time; moldable, as by injection molding or the like; and steady-state in that it does not exhibit significant loss of stiffness under a continuous load, allowing neck 104 and plug 102 to maintain an effective force toward the ear canal 26. Desirably, a material such as polyethylene is used. However, it is contemplated that the ear clip portion of hearing protector 100 may be manufactured from nylon, plastics such as polypropylene, polyvinyl chloride, polycarbonate; metals such as titanium, steel, or aluminum composites; or elastomer such as silicon, thermoplastic elastomer (TPE), polyurethane rubber, ethylene propylene rubber, or a combination thereof.

Referring to FIG. 7, a plug 102 is connected to the neck 104. The ear plug 102 may be a separate button of a flexible material as described below, shaped so that it is sufficiently seats against the concha 24, tragus 20 and anti-tragus 22 surrounding the entrance to the ear canal 26. Plug 102, when functioning as a cap (FIG. 3) may be of a generally hemispherical shape and has a diameter somewhat greater than that of the average adult human ear canal, or another rounded shape.

For semi-insert or full-insert plugs (FIGS. 4-5), the plug 102 of the invention may be substantially cylindrical in shape and have a diameter somewhat greater than that of the average adult human ear canal. For instance, a diameter of between about 7 cm and about 15 cm is generally acceptable. Desirably, the diameter of the earplug will be between 8 cm and 14 cm. Further, it should be noted and understood that the term "cylindrical" as employed herein includes within its scope structures having a relatively shallow truncated cone shape or a substantially spherical shape. Where the earplug takes the form of a truncated cone, the above diameter criteria may be taken at the midpoint of the cone. Where the earplug is spherical, the above criteria may be applied to the diameter of said sphere.

Plug 102 may be connected to neck 104 in a variety of ways. A first exemplary embodiment of a plug-neck connection, shown in FIG. 8B, has a stem 120 that is placed a corresponding cavity 122 in plug 102. This type of arrangement may allow the wearer to change only the plug 102, and reuse the remaining portion of the hearing protector 100. If the stem 120 is long enough to fit at least partially into the ear canal 26 (FIG. 4 or 5), the stem 104 is preferably flexible so that it flexes as the wearer adjusts the hearing protective device. A non-pliable stem may cause discomfort as the wearer adjusts the hearing protection device. To provide a secure fit in the cavity 122, the stem 120 may be made from a compressible, resilient material and have a width dimension slightly larger than the width dimension of cavity 122; when the stem 120 is positioned in cavity 122, the stem 104 will press against the wall defining cavity 122 to provide a friction fit. It is further contemplated that a more permanent connection between stem 120 and plug 102 may be achieved with an adhesive. Adhesives such as hot-melt glue, cyanoacrylate glue, casein glue, cement glue, resin glue would be suitable for this purpose.

Figure 8A:
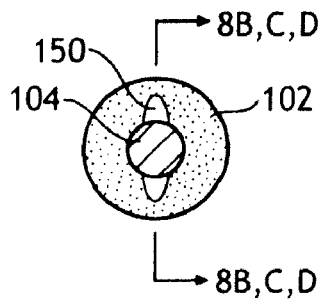
FIG. 8A is a partial cross section of the hearing protector of FIG. 7, taken at the plane defined by line 8A-8A.
Figure 8B:
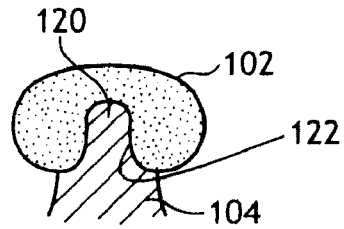
FIG. 8B is a partial cross-section of the hearing protector of FIG. 8A, showing one embodiment of the plug member attachment to the stem, and taken at the plane defined by line 8BCD-8BCD.
Figure 8C:
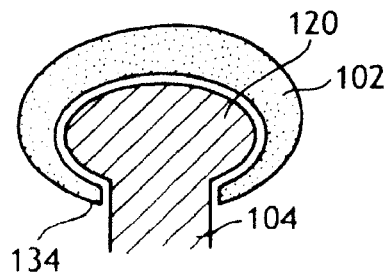
FIG. 8C is a partial cross-section of the hearing protector of FIG. 8A, showing one embodiment of the plug member attachment to the stem, and taken at the plane defined by line 8BCD-8BCD.

In a second exemplary embodiment of a plug-neck connection, shown in FIG. 8C, the neck 104 has a mushroom-shaped stem 130. A plug 102 having a corresponding mushroom-shaped cavity 132 therein is disposed over stem 130. Desirably, there is enough tension in the annulus 134 at the entrance of the cavity 132 to keep the plug 102 from slipping off of the stem 130 as the hearing protector is adjusted within or removed from the ear.

Figure 8D:
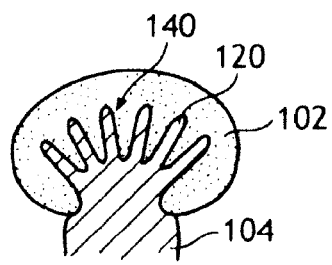
FIG. 8D is a partial cross-section of the hearing protector of FIG. 8A, showing one embodiment of the plug member attachment to the stem, and taken at the plane defined by line 8BCD-8BCD.

In a third exemplary embodiment of a plug-neck connection, shown in FIG. 8D, the neck 104 has a flanged end 140. A plug 102 is adhesively connected to the flanged end 140 by an adhesive as previously described for the stem of FIG. 8B and/or a mechanical connection.

It is to be understood that the particular compound for making plug 102 is less important than the mechanical qualities of the plug 102. Most desirably, the earplug, when deformed, will tend to recover its original shape and size. The conformity of the foamed polymeric composition will create a seal against the ear wall to block sound from entering into ear canal. The principal characteristics exhibited by the ear plug materials are that it is soft and pliable to conform to the shape of the ear canal and ear canal entrance.

In one embodiment, the plug 102 material may have a skin formed on its outer surface, with the skin broken to permit the venting of the ear canal (not shown). With the open-cell construction of the plug 102, air may slowly escape from the ear canal to the surrounding atmosphere until the pressures are equalized. If the atmospheric pressure increases, the pressure within the ear canal may again be equalized to eliminate dizziness, vertigo, or other discomfort. It will be realized that the rate of flow of air through the open cell foam will be relatively slow and hence, the pressure equalization will not in any way affect the sound attenuating properties of the hearing protector 100.

In each of the exemplary embodiments described herein, the plug 102 may be made from dynamically stiff foam. One suitable dynamically stiff foam is described in U.S. Pat. No. 5,420,381, the contents of which are incorporated herein by reference to the extent they are consistent with the present invention. Alternatively, the plug 102 may comprise any other conventional earplug foam material such as the foam disclosed in U.S. Reissue Pat. No. 29,487, all of the contents of which are also incorporated herein by reference to the extent it is consistent with the present invention. In yet another embodiment, plug 102 may be made from silicon rubber. However, it is noted that any flexible polymeric material which can be foamed so as to result in a formed plug structure meeting the design criteria set forth herein constitutes a satisfactory material of construction in the plugs 102 of the invention. Accordingly, polymers of ethylene, propylene, vinyl chloride, vinyl acetate, diisocyanate, cellulose acetate or isobutylene can all be generally employed.

The neck 104 may have a solid cross-section as seen in FIG. 8A. Desirably, neck 104 is substantially cylindrical in shape, but may have other shapes that fit into the concha 24, between the tragus 20 and anti-tragus 22. A flange 150 may provide strength to the junction between the shoulder 106 or handle 110 and the neck 104. However, the precise shape of the neck and flange may be greatly influenced by aesthetic design, and it is contemplated that other shapes would be suitable, as evidenced by the other embodiments of hearing protector 100 described herein.

Shoulder 106 is a section of the hearing protector 100 that will experience relatively high stress as compared to the neck 104 and the arm 108. Shoulder 106, operates as the spring member of hearing protector 100. With respect to a reference plane that lies along line 8A-8A of FIG. 7, and 8BCD-8BCD of FIG. 8A, shoulder 106 operates to project arm 108 away from the reference plane. When the hearing protector 100 is clipped about the pinna 12, the arm 108 is forced in a direction toward the reference plane. In this regard, the shoulder 106 operates as a partial helical spring. The shoulder 106 is then under stress, and it too, may flex closer toward the reference plane. The hearing protector 100 appears more flattened which in use, and is in a stressed state (see FIG. 6). Shoulder 106 may have a curved appearance when viewed from the side, similar to the embodiment shown in FIG. 12. However, it is contemplated various other curvatures or aesthetic shapes may be incorporated into the shoulder 106 shape without affecting functionality.

Handle 110 is an optional feature that enables a user to conveniently grip the hearing protector 100 to spread the bow member for attachment to the ear. Handle 100 may also be used to temporarily pull the plug 102 away from the ear canal 26 or adjust the position of plug 102. Handle 110 is generally an elongated shape. However, as it is only used as a handle and may not experience as much stress as other sections of hearing protector 100, handle 110 may incorporate many aesthetic features without affecting its function. For example, a separate material 160 may be overlaid onto or otherwise attached to handle 110 to add visual interest and/or a different tactile feature. It is contemplated that handle 110 may be constructed from a unitary member.

Arm 108 is a flexible member that curves about pinna 12 from about junction 170 (where the helix 16 meets the head tissue 36) to the back of the pinna (see FIGS. 1 and 2). Desirably, the distal end 172 (FIG. 7) may hang down near the lobe 14, or even partially wrap around the concha 24. This configuration makes it easier to remove and replace the hearing protector 100 onto the ear. Also desirably, the distal end is rounded so as to increase comfort.

As mentioned previously, the neck 104, shoulder 106, and arm 108 may be constructed as a unitary piece, as by injection molding. However, it is contemplated that these regions could include one or more parts or over-molded pieces, similar to the embodiments of FIGS. 9-12, as discussed herein.

In operation, the device of FIGS. 6-7 is biased toward the ear so that the neck 104 will press the plug 102 inward toward a position capping the ear canal 26. To apply the hearing protector of FIG. 7, the arm 108 is placed behind the pinna 12 so that is rests against a portion of pinna 12 such as the concha 24, and the head tissue 36. The wearer disposes the plug 102 into or over the entrance of the ear canal 26. When the hearing protector is applied in this manner, it appears more flattened, as in FIG. 6. The neck 104 and plug 102, by bearing against the portion of the ear surrounding the entrance to the canal, reduces the amount of sound that is transmitted along the canal and also reduces the sound transmitted by the flesh and bone structure to the middle and inner ear. The hearing protector 100 shown FIG. 3, while aesthetically different, operates in the same manner.

A second exemplary embodiment of the hearing protector 100, shown in FIGS. 9-10, is assembled from several separate parts. Generally, the hearing protector 100 of this embodiment operates the same way, but provides more opportunity for aesthetic enhancement and for optimizing strength properties in particular regions of hearing protector 100, such as the shoulder 106. This may provide opportunity to provide a higher performance hearing protector 100 at a lower cost. As may be seen, the overall shape of the hearing protector is more angular. This may be purely aesthetic, or be due to the use of a straight component, as described herein.

In this particular embodiment, a first component is the neck 104 and a portion of the shoulder 106, which collectively define an elbow 180. A second component is a spring 184, which is a member that functions as a torsion spring. A third component is the arm 108 and integrally-connected partial-sleeve 182. Sleeve 182 overlaps a portion of the shoulder region 106 where it connects to spring 184. Yet a fourth component is the plug 102, that attaches to the neck in the way described in the previous embodiment.

The neck 104 and shoulder 106 may be constructed from a molded plastic such as polyethylene, polypropylene, polyvinyl chloride, polycarbonate, and the like. Arm 108, along with integral sleeve 182, is desirably a flexible member manufactured from the same type of materials described for the embodiment shown in FIG. 6. The spring 184 may be constructed from various metals or composite materials, for example, spring steel.

Desirably, elbow 180 is an L-shaped member having a short leg 190 and a long leg 192. Short leg 190 and long leg 192 may merge at approximately an angle 194 ranging from about 85 to 90 degrees. The short leg 190 includes a straight section for receiving the spring 184. The long leg 192 may be straight as shown, or more curved.

As compared to the neck 104 and corresponding plug 102 of the previous embodiment (FIG. 6), the neck 104 and plug 102 may have a rectangular or other angular shape that fits between the tragus 20 and anti-tragus 22 to cover the ear canal 26. However, it is contemplated that the neck 104 of this particular embodiment may be round, oval, or any shape that functions to adequately cover the ear canal 26.

Torsion spring 184 may be permanently attached to the elbow 180 and sleeve 182 with an adhesive such as cyanoacrylate glue, casein glue, cement glues, resin glues. In the alternative, such connections may be made with an interference fit between the members.

Referring still to FIG. 10, in another embodiment of the present invention, the hearing protector 100 may differ from the previous embodiment by attaching the spring 184 to elbow 180 with a rotating connection. While the rotating connection may allow the elbow 180 to freely rotate with respect to spring 184, it is desirable that an increased resistance to rotation is experienced when the plug 102 is placed in or against the ear canal. This is to maintain adequate pressure against between the plug 102 and ear canal 26 opening, and thus, prevent plug 102 from falling away from the ear canal during use. The increased resistance may be achieved by a detent located between the spring 184 and the elbow 180. In the alternative, the increased resistance may be achieved other ways, such as by a screw thread. Regardless of the exact structure used to create increased resistance, it will likely be caused by material interference between the spring 184 and elbow 180. It is further contemplated that the spring 184 in this particular embodiment may be stiff enough to be ineffective as an actual spring.

Referring still to FIG. 10, in yet another embodiment of the present invention, the hearing protector 100 may be constructed from a flexible, semi-rigid unitary member (similar to the embodiment of FIG. 6) that is reinforced and/or aesthetically enhanced with additional components. In this embodiment, the shoulder region 106 is partly defined by an elbow member 180. The elbow member may merely be a cover constructed from a plastic or rubber type material, and may be the same in appearance or feel, or may be different. Likewise, sleeve member 182 used to cover the arm 108, and may extend to partially cover the shoulder 106 as shown. The sleeve member may be a cover constructed from a plastic or rubber type material, which may be the same in appearance or feel, or may be different. The section of shoulder 106 located between elbow member 180 and sleeve 182 may be relatively straight for aesthetic reasons.

In another exemplary embodiment of the present invention, shown in FIGS. 11 and 12, hearing protector 100 may be of unitary construction, or may be constructed from three separate components. Desirably, the three components include a plug 102/neck 104; a shoulder 106; and an arm 108. In this embodiment, the plug 102 may like that described for the previous embodiments. The neck 104 may be integrally connected to the shoulder 106, which are formed from a rigid plastic such as polyethylene, polypropylene, polyvinyl chloride, and polycarbonate. Desirably, the arm 108 is attached to an end of the shoulder 106 opposite the neck 104.

Arm 108 may be the flexible plastic material as described for the embodiment of FIG. 6. Desirably, arm 108 is a relatively soft, pliable rubber-like material that is reinforced with an embedded stiffening wire. Arm 108 is joined to the end of shoulder 106 by an adhesive such as cyanoacrylate glue, casein glue, cement glues, resin glues. The stiffening wire is partially embedded into shoulder 106 for additional strength at this joint.

Additional embodiments of the hearing protector 100 of the present invention are depicted in FIGS. 13-25. These embodiments differ from the previous embodiments in that they may replace the ear plug 102 with a specially shaped pad that generally covers the ear canal 26 and a portion of the surrounding concha 24. This pad is referred to as an EAM pad 200. (The term "EAM" is an acronym for "external auditory meatus.") Further, force may be solely or partially applied to the EAM pad 200 by a pressure pad 202, as described below. This force will create pressure between the EAM pad 200 and the concha 24. It is contemplated that additional pressure, beyond that provided by the pressure pad 202, may be obtained by using the previously described biased bow member in conjunction with the pressure pad 202. However, the bow member is optional, as well as the handle 110. In some embodiments, a target indicia located on an exposed pressure plate 208 may aid in positioning the EAM pad 200 and pressure pad 202. Further, a touch indicia located on the optional handle and/or bow will indicate to the wearer where to touch to position the hearing protector 100.

Figure 14:
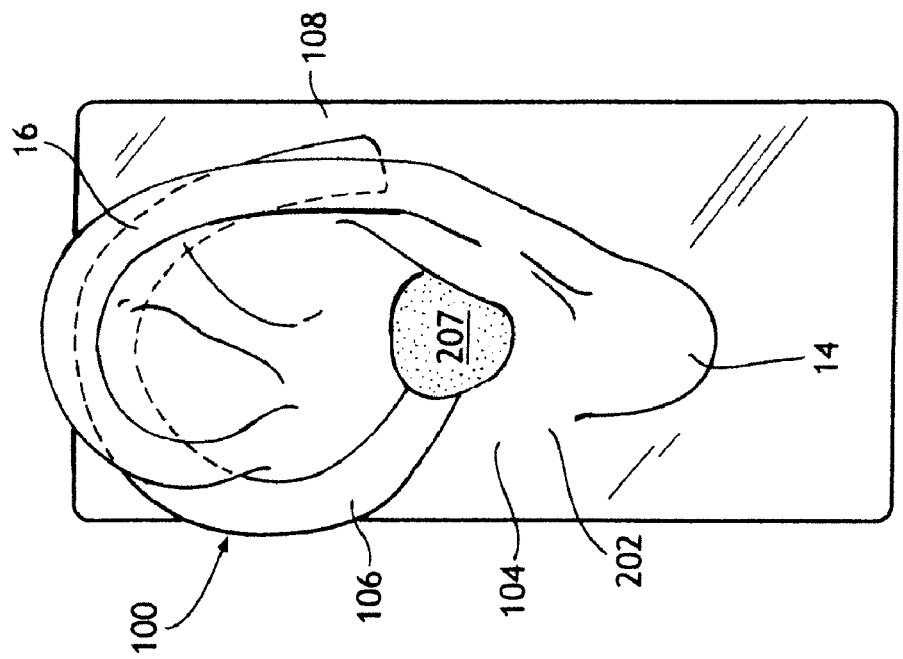
FIG. 14 is a side perspective view of yet another embodiment of the hearing protector of the present invention as it would appear when engaging an ear.
Figure 15:
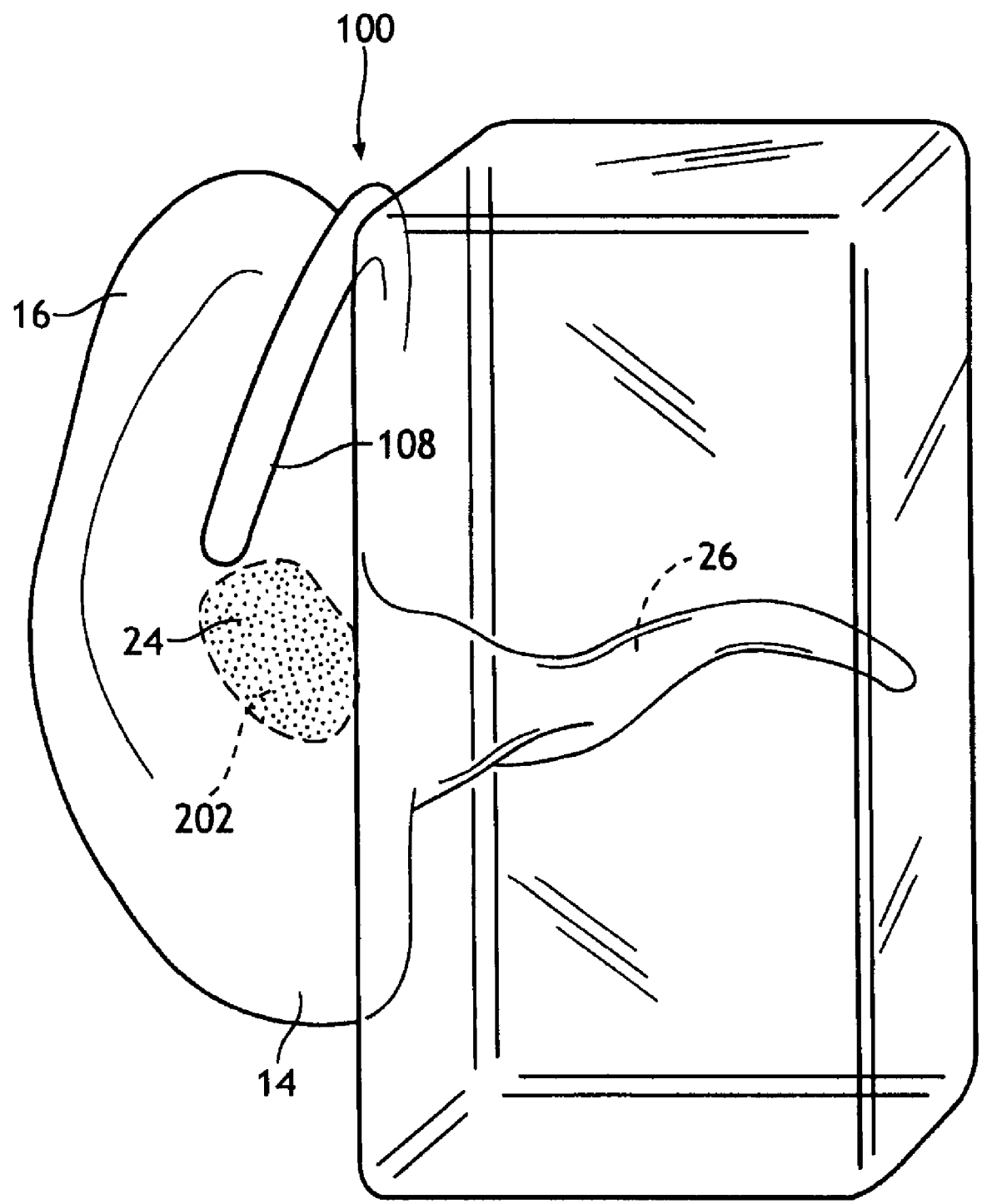
FIG. 15 is a rear perspective view of the hearing protector of FIG. 14.
Figure 16:
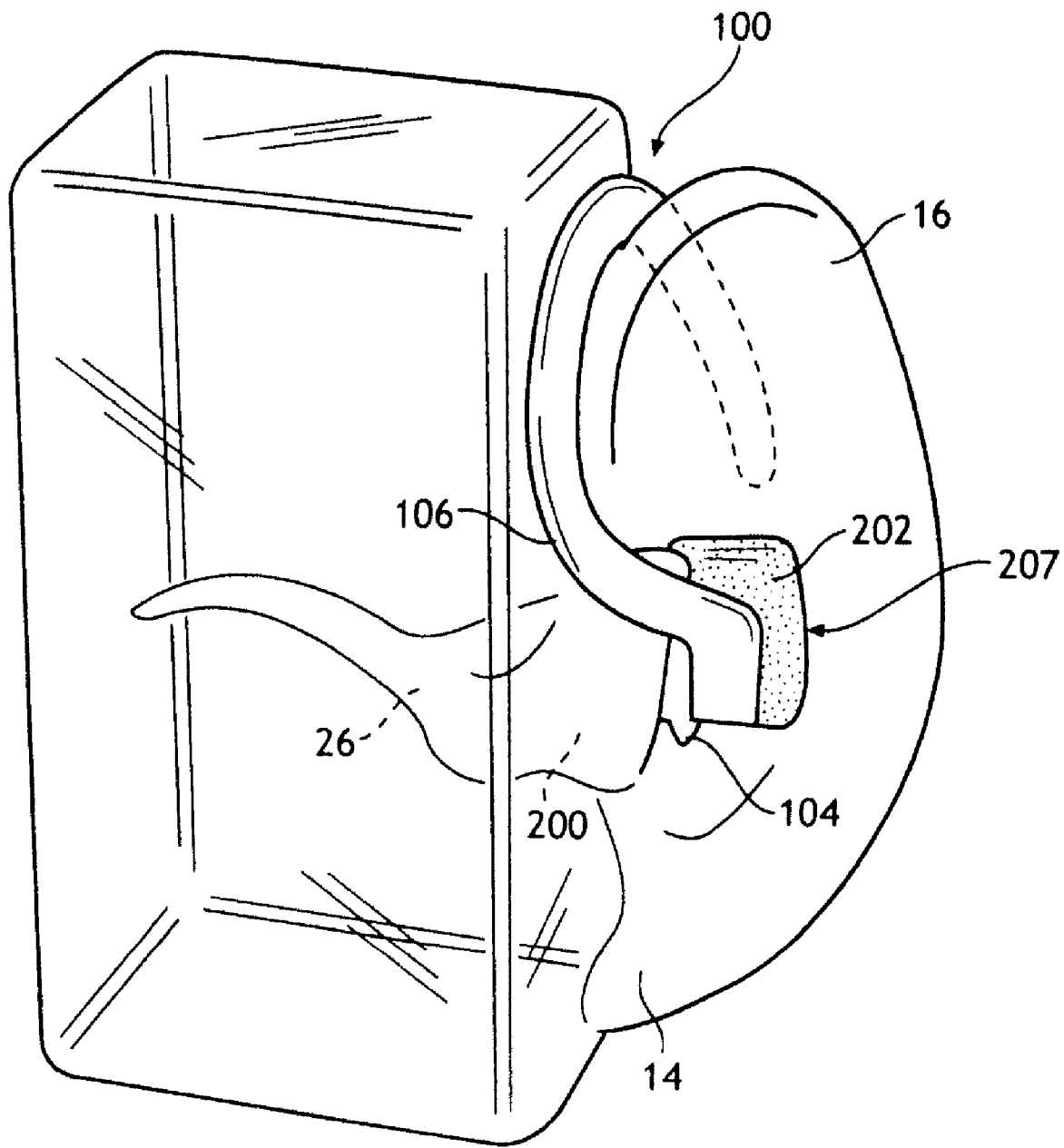
FIG. 16 is a front perspective view of the hearing protector of FIG. 14.
Figure 17:
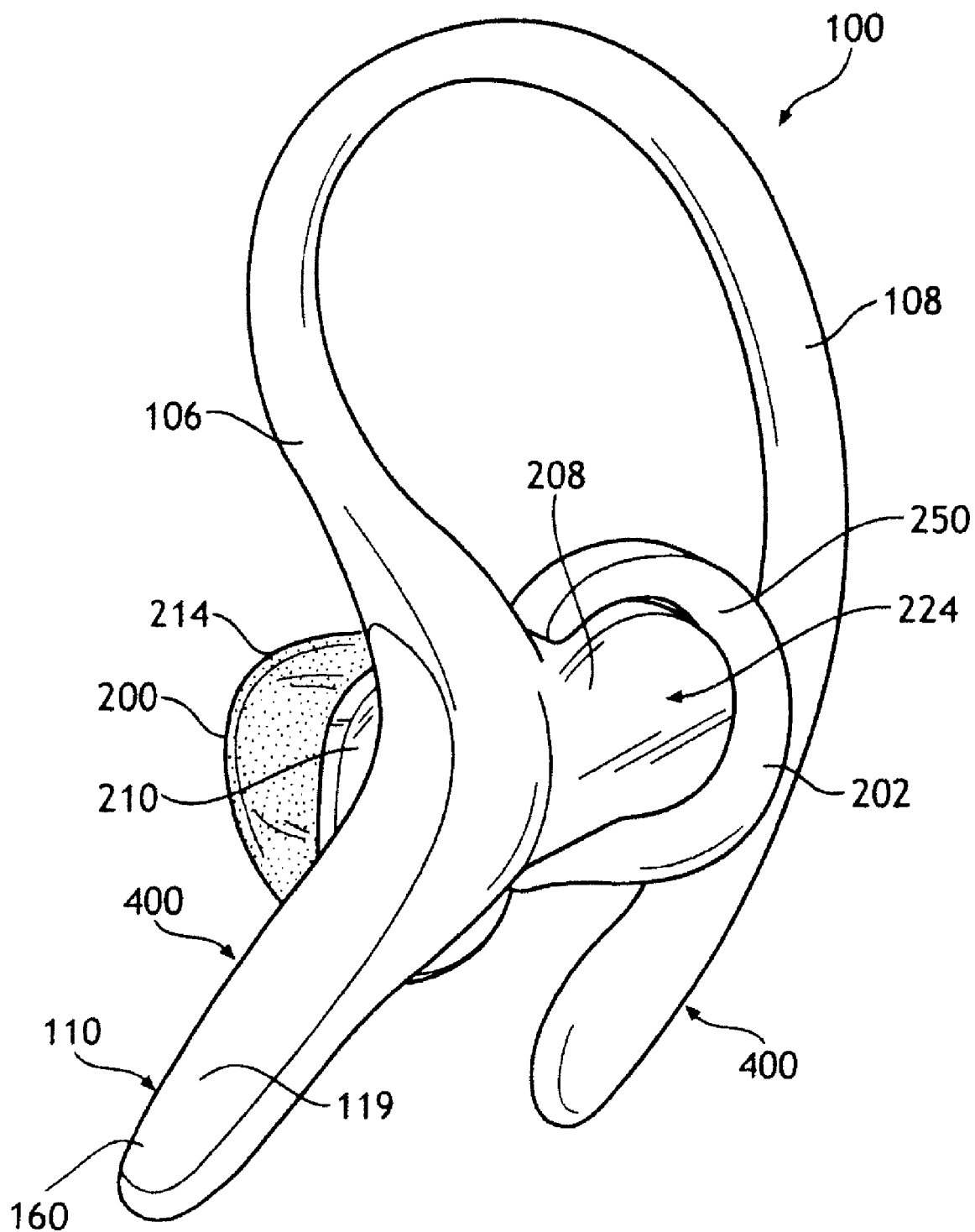
FIG. 17 is a side perspective view of a seventh embodiment of the hearing protector of the present invention.

Referring now to the embodiments of FIGS. 13-16, the hearing protector 100 may be completely unitary in construction, or may be assembled from two or more separate parts. For instance, FIG. 13A depicts a separate EAM pad 200 connected to a neck 104. EAM pad 200 is a pliable member that may conform to a portion of the external auditory meatus. The pressure pad 202 is connected to the shoulder 106 (FIG. 13A) or to an opposite surface of the neck 104 (FIGS. 14-16). The pressure pad 202 cooperates with the concha 24 to apply force to the EAM pad 200 so that it maintains a desired position with respect to ear canal 26, and may desirably, effect a seal between the pad 200 and concha 24 and/or ear canal 26.

Figure 13B:
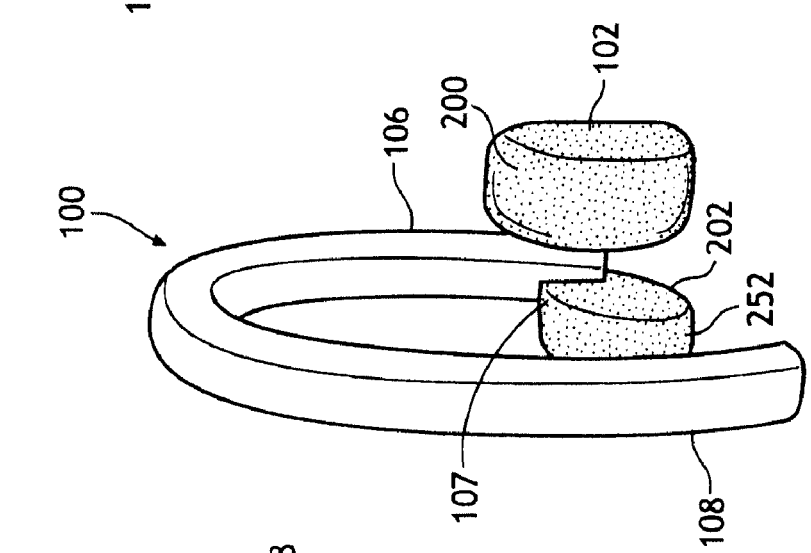
FIG. 13B is a rear perspective view of the hearing protector shown in FIG. 13A.
Figure 13A:
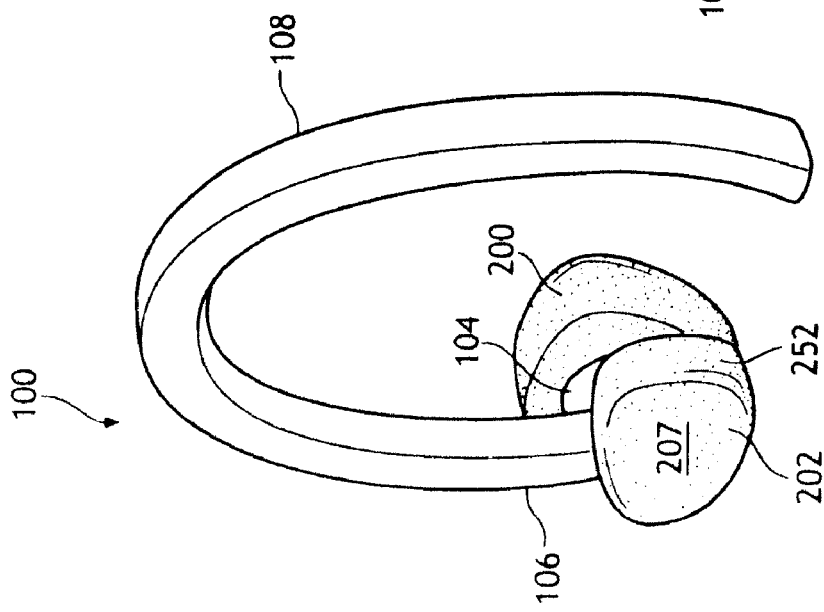
FIG. 13A is a side perspective view of another embodiment of the hearing protector of the present invention.

The neck 104 may extend from a side of shoulder 106 or another surface thereof, such as the bottom edge 107 referenced in FIG. 13B. The neck 104, regardless as to its orientation with respect to shoulder 106, acts as a hub for EAM pad 200, and possibly, for pressure pad 202. Pressure pad 202 may instead be directly attached to the shoulder 106 and not directly attached to neck 104 (see FIGS. 13A and 13B).

Together, the shoulder 106 and arm 108 form the bow member that generally extends from the tragus 20, upward to where helix 16 meets tissue 36, and down around the pinna 12 adjacent to where concha 24 meets tissue 36. The arm 108 may or may not continue to wrap around and contact the lobe 14.

The EAM pad 200 and pressure pad 202 may be made from materials having the same or different physical and/or strength characteristics. In particular, the pads 200 and 202 may have the same or different elastic properties, density, compression strength, etc. Pads 200 and 202 may even have a unitary structure (not shown). Desirably, however, the EAM pad 200 is easier to compress and thus more conformable to the ear than the pressure pad 202. This strength property difference may be measured using a standardized test method to determine foam compression, e.g. Standard Test Methods for Flexible Cellular Materials—Slab, Bonded, and Molded Urethane Foams, ASTM-D-3574, American Society for Testing and Materials International, 2005, incorporated herein by reference to the extent it does not conflict with the present invention.

Appropriate materials from which the pads 200 and 202 may be made include all the foams previously listed for plug 102. In addition, the pads 200 and 202 may be constructed from other compliant elastic materials such as silicone, rubber, and the like, regardless of whether or not they have a foam cell-structure. In one embodiment, pad 200 is a foam material as described above, and pad 202 is constructed from a silicone material. Rubber and silicone materials may be characterized by hardness measurements such as those that may be obtained by using the following test method incorporated herein to the extent it is consistent with the present invention: Standard Test for Rubber Property-Durometer Hardness, ASTM 2240-05, American Society of Testing and Materials International, 2005. Desirably, the pressure pad 202 may be of greater hardness than the EAM pad 200.

In another and possibly more cost effective embodiment, pads 200 and 202 are made from the same material, and may even be integrally connected. The term "integral" is used herein to mean that two or more parts have a homogenous or continuous connection therebetween. The term unitary is used herein to mean a direct, permanent connection that connects more than one part, such as by adhesion, fusing, welding, or the like. For example, the neck 104 could extend from the bottom surface of shoulder 106, and unitary pad 200/202 could extend outwardly from each side of neck 104 and shoulder 106. In one example, the pads 200/202 could be similar to the separate pads 200 and 202 shown in FIG. 13B, except that the volume between the separate pads could be bridged with a material, either the same as or different to either or both pads 200 and 202. This bridging material may have an integral or non-integral connection between the pads 200 and 202. Non-integral connections include permanent welded, fused, or adhesive connections, and the like.

Figure 19:
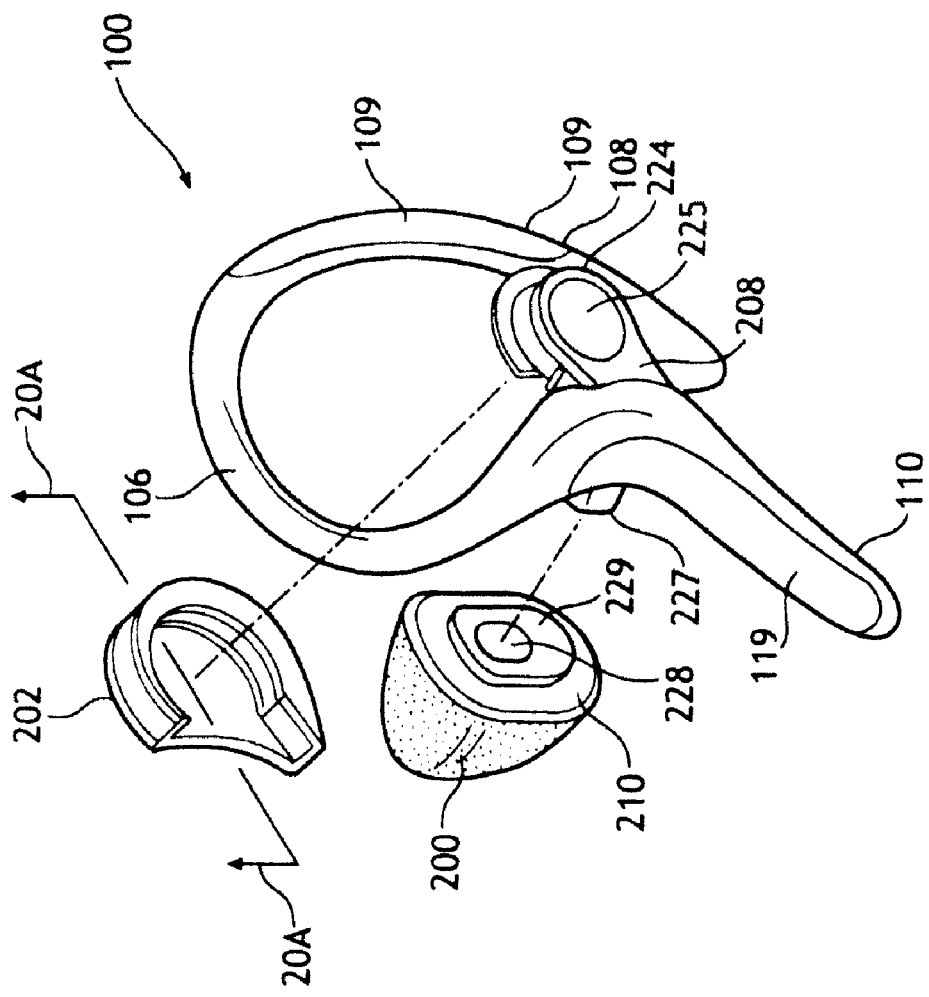
FIG. 19 is an exploded view of the hearing protector shown in FIG. 17.
Figure 18:
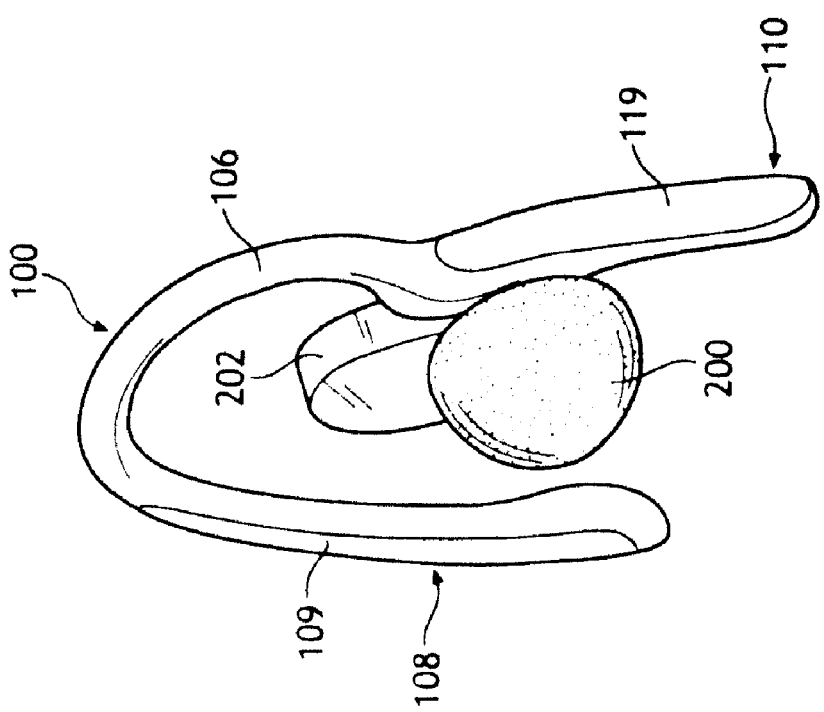
FIG. 18 is an opposite side perspective view of the hearing protector of FIG. 17.

Most desirably, the EAM pad 200 is shaped so that it may be substantially or fully disposed against a human ear canal. While human anatomy may vary between persons, the conformity of the material from which the pad is made will be able to compensate for most variances, and thus will be comfortable for most persons. However, it is contemplated that the EAM pad 200 could be made available in different sizes to achieve a more custom-like fit. The shape of the EAM pad 200 may somewhat resemble an elliptical dome with a nearly elliptical-shaped footprint visible at flat side surface 210 (FIG. 19). The EAM pad can be configured to partially or fully engage or be disposed against the ear canal, such as with ear caps or semi- and full-insert plugs.

So that the EAM pad 200 effects a seal against the ear canal, there are no creases, cavities or pockets on the domal surface 214. Desirably, the material from which the EAM pad is constructed has a skin on its outer surface to so that it may be easier to clean the surface for repeated use. The seal against the ear may not be perfect due to skin texture or hairs on the external auditory meatus. However, the seal is effective enough to prevent significant sound energy from entering the ear canal.

Pressure pad 202, unlike the EAM pad 200, does not need to create a seal for noise control, but some sound attenuation may occur by its presence. The primary function of pressure pad 202 is to apply force to the EAM pad 200 to remain partially or fully engaged with or disposed against the ear canal 26. In use, the pressure pad 202 is compressed between the concha 24 and the neck 104, see FIGS. 15 and 16. Because the concha 24 is not aligned with the ear canal 26 as viewed from a side (FIGS. 13-14), the pressure pad 202 may be offset from the EAM pad 200.

Desirably, the pressure pad 202 is attached to a pressure plate 208 that extends from shoulder 106 adjacent the neck 104. Pressure plate 208 may be a blade-like structure that extends from the shoulder or neck (see FIG. 20). Desirably, pressure plate 208 is part of the unitary ear clip structure, and is rigid enough so that it does not bend significantly when pressed in order to adjust the fit of the EAM pad 200 and/or pressure pad 202. In another embodiment, the pressure plate 208 may be selectively removable as described herein.

The pressure pad 202 may be shaped for comfort, and if desired, for aesthetics. For reasons of comfort, the edges 252 (see FIG. 13B) may be rounded to mitigate or create fewer pressure points on the pinna and concha areas of the ear respectively. For reasons of aesthetics, it is contemplated that there may be a pattern or indicia printed or exhibited as a relief on the outer surface 207 of pressure pad 202. Desirably, in this particular embodiment of the present invention, the shape of the pressure pad 202 may be a roughly oval or circular discoid, and may be made as small as possible to reduce material costs, while at the same time serving to create the desired pressure between the neck 104 and concha 24.

EAM pad 200 may connect to neck 104 in a variety of ways, such as the methods depicted in FIGS. 8A-8D. Further, the EAM pad 200 be connected to neck 104 by a ball and socket, hook and loop, magnets, adhesive, or any other connection that may be selectively undone by the user. For instance, the neck may be connected to a stem with a ball-shaped receiver or other connections as described below with respect to FIG. 19.

The thickness of the pad 200 may be lesser or greater than is shown, and is dependent on the stiffness of the material used for the pad. Desirably, the EAM pad 200 is thick enough so that the wearer cannot detect any rigid plastic portions such as the neck 104 or anything protruding therefrom.

Shoulder 106 is a section of the hearing protector 100 that will likely experience various stresses as it is bent for placement about the pinna. While in this particular embodiment shoulder 106 is not stressed significantly after it is in place about the pinna, it is contemplated that in other embodiments, shoulder 106 may operate in part as the spring member of hearing protector 100. Shoulder 106 may have a curved appearance when viewed from the side, similar to the embodiment shown in FIG. 12. However, it is contemplated various other curvatures or aesthetic shapes may be incorporated into the shoulder 106 shape without affecting functionality.

In FIGS. 17-20, yet another embodiment of the hearing protector 100 is depicted. This embodiment generally differs from that shown in FIG. 13 in several ways. First, it includes an optional handle 110. As described above, handle 110 may include a material overlay 109 for functional or aesthetic purposes. Second, hearing protector 100 may include an exposed pressure plate 208 onto which the corresponding pressure pad 202 is attached. Third, the arm 108 may include an optional material overlay 119 for functional or aesthetic purposes. The bow member is similar to that shown in the embodiment of FIG. 6, except that the bow member may not act as a torsion spring. The EAM pad 200 may be identical to that shown in the embodiment of FIG. 13.

Optional touch indicia 400 may be located on the optional handle 110 and/or bow member 108 and serve to indicate where the user should touch the hearing protector 100 for the positioning thereof. The touch indicia may be defined by a different material, color, texture, and/or symbols. For example, the overlays 109 and 119 define a touch indicia 400 for the embodiment shown in FIG. 20. Touch indicia may look and/or feel different to the user.

Figure 20:
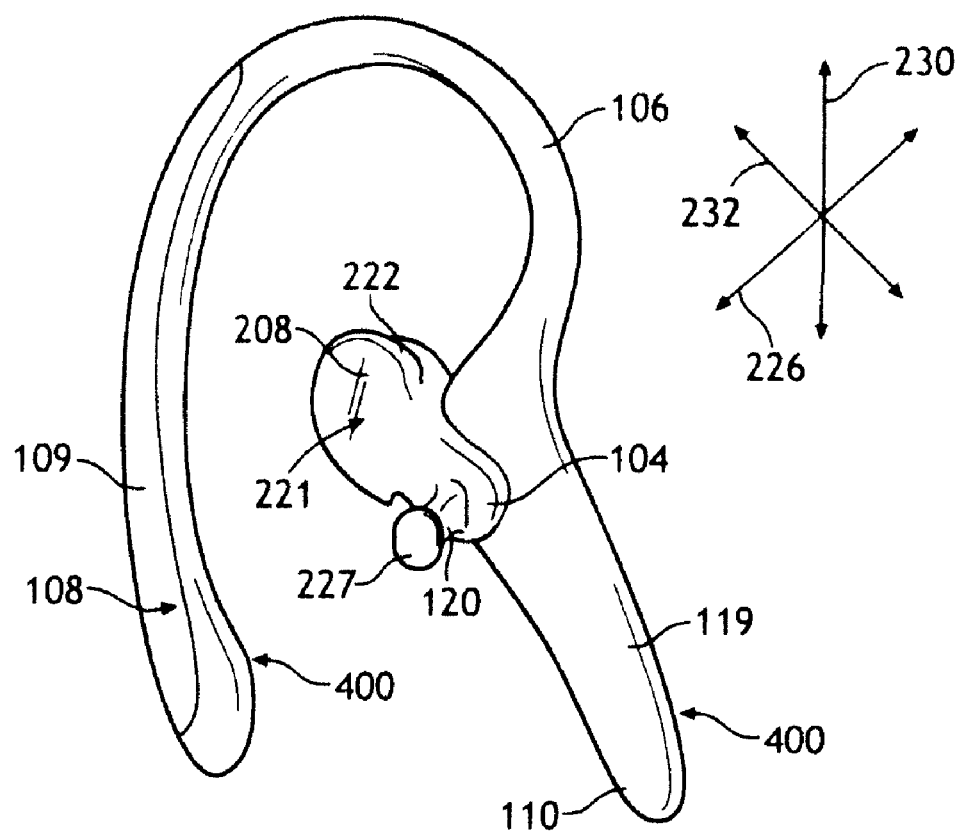
FIG. 20 is a partial perspective view of the hearing protector shown in FIG. 18, minus the pressure pad and the EAM pad.
Figure 20A:
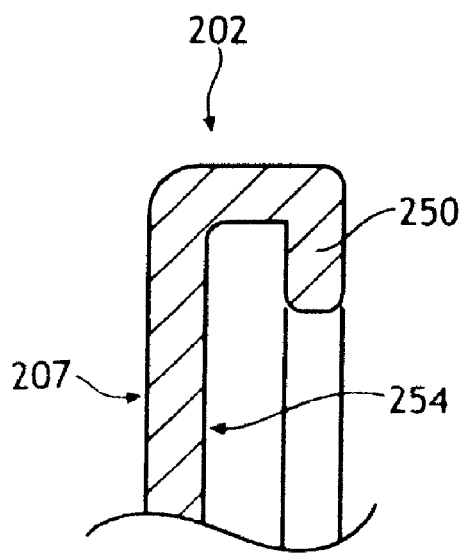
FIG. 20A a partial cross section of the pressure pad taken at lines 20A-20A of FIG. 19.

Referring to FIG. 20, the pressure plate 208 extends from neck 104, and is oriented perpendicularly with respect to the stem 120 in both the x-direction 226 and y-direction 232. In one embodiment, there is an integral connection between neck 104 and pressure plate 208. The portion of shoulder 106 in the immediate vicinity of the pressure plate 208 is generally oriented in z-direction 230. In another embodiment (not shown) pressure plate 208 may be detached and replaced from the ear clip structure. For example, a replacement unit defined by a pressure pad 202 and corresponding pressure plate 208 may be selectively detached and replaced from the neck 104 or shoulder 106. It is contemplated that the connection may include a ball and socket, hook and loop, magnets, adhesive, or any other connection that may be selectively operated by the user.

Pressure plate 208 may have a rounded shape such as a hemi-discoid shaped body, shown. On the outer plate surface 221 of the pressure plate 208 (which will face the ear when in use), there may extend a flange 222. Flange 222 may be an arcuate shape or any shape that corresponds to the shape of EAM pad 200.

Referring to FIG. 19, the pressure-plate face 224 (opposite to surface 221) may have a surface indicia such as an exposed flat surface or a patterned surface. For instance, as seen in FIG. 19, the face 224 includes a surface indicia in the form of a detent 225 to indicate to a user that this is an area to which pressure may be applied with a finger to adjust the EAM pad or the pressure pad. While a circular detent 225 is depicted in this exemplary embodiment, any texture, pattern or indicia may be used for this purpose, such as a raised pattern or color indicator.

Stem 120 may have a ball-shaped receiver 227 that corresponds to a socket feature 228 on the EAM pad 200. Preferably the socket feature 228 is defined by a cavity in a separate frame member 229 that engages the stem 120 and ball-shaped receiver 227. The EAM pad 200 is affixed to the frame member 229 in the ways described previously with respect to FIGS. 8A-D. The separate frame member 229 may be made of materials similar to the hearing protection device 100, but may also be made of a soft flexible material. However, any other connection between neck 104 and EAM pad 200 may be used (e.g. hook and loop, magnets, adhesives, and the like).

The pressure pad 202 of FIGS. 17-20A is different from the embodiment of FIG. 13 in that desirably, it wraps only partially about a pressure plate 208 in order to leave a portion of the pressure plate exposed. The pressure pad 202 has the same general shape as the pressure plate 208 when viewed from the x-direction 226. As seen best in FIG. 20A, a lip 250 extends from the outer face 207 of the pressure pad 202, the lip 250 being configured to wrap about the flange 222 on pressure plate 208. The inner face 254 of pressure pad 202 may make direct contact with the pressure plate outer surface 221, or may include an adhesive material therebetween.

For any of the embodiments shown in FIGS. 13A-25, the EAM pad 200 and the pressure pad 202 may be made of the same material (e.g. viscoelastic foam) and characterized by one or more material properties. For example, the density of the EAM pad 200 and the pressure pad 202 may be about 6 [96.1 Kg/m$^3$] to about 20 lbm/ft$^3$ [320.4 Kg/m$^3$]. More desirably, the density of the EAM pad 200 and the pressure pad may be about 10 [160.2 Kg/m$^3$] to about 15 lbm/ft$^3$ [240.3 Kg/m$^3$] (see ASTM 3574-05, previously incorporated). The compression force deflection at 25 percent (see, ASTM 3574-05, previously incorporated) is desirably between about 0.3 psi [0.02 Kg/cm$^2$] to about 10.0 psi [0.73 Kg/cm$^2$], and more desirably between about 0.3 psi [0.02 Kg/cm$^2$] and about 4.0 psi [0.29 Kg/cm$^2$]. The foam can further be described by cell size which may be determined using the following test method incorporated herein to the extent it is consistent with the present invention: Standard Test Method for Open-Celled Content of Rigid Cellular Plastics by the Air Pycnometer, ASTM 2856-9.4, American Society of Testing and Materials, Annual Book of ASTM Standards, 1998. Desirably, the cell size is a minimum of about 80 pores per inch, and more desirably a minimum of about 100 pores per inch. The cell structure may be further defined as having between about 30 percent to about 70 percent open cells, and more desirably between about 40 percent to about 60 percent open cells. In addition, the recovery time for the foam material may be desirably between about 2 seconds to about 120 seconds, but more desirably be between about 2 seconds to about 20 seconds. See, ASTM D 3574-05, infra. Furthermore, the water absorption of the foam may desirably be less than about 20 percent, and more desirably, less than about 5 percent as measured by test method incorporated herein to the extent it is consistent with the present invention: Standard Test for Water Absorption 24 Hour/Equilibrium, ASTM D570, American Society of Testing and Materials.

For any of the embodiments shown in FIGS. 13A-25, the pressure pad 202 may be made of different materials than the foam used to construct EAM pad 200. For example, the pressure pad 202 may be described as an open cell or reticulated foam material which may be characterized by several material properties as determined by the test methods noted above. When reticulated foam is used as the pressure pad 202, the density of the foam may be about 1.2 to about 2.6 lbm/ft$^3$ [19.2 to 41.6 Kg/m$^3$]. More desirably, the density of both the EAM pad 200 and the pressure pad 202 may be about 1.5 to about 1.9 lbm/ft$^3$ [24.0 to 30.4 Kg/m$^3$]. The compression force deflection at 25 percent is desirably between about 0.4 to about 2.0 psi [0.03 to 0.14 Kg/cm$^2$], and more desirably between about 0.65 to about 1.2 psi [0.04 to 0.08 Kg/cm$^2$]. The foam may further be described by the cell size, and desirably has a cell size between about 40 to about 80 pores per inch, and more desirably between about 50 and about 70 pores per inch. The cell structure may desirably have between about 40 to about 80 percent open cells, and more desirably between about 50 to about 70 percent open cells. The recovery time for the foam material may be desirably between about 1 second to about 20 seconds, and more desirably be between about 2 seconds to about 4 seconds. The water absorption of the foam may be desirably less than about 20 percent, and more desirably less than about 5 percent.

Desirably, the thickness of the pad as measured between the outer face 207 and inner face 254 may be about 0.5 to about 6.0 mm. More desirably, the thickness of the pad as measured between the outer face 207 and inner face 254 may be about 1.0 to about 3.0 mm.

Figure 21:
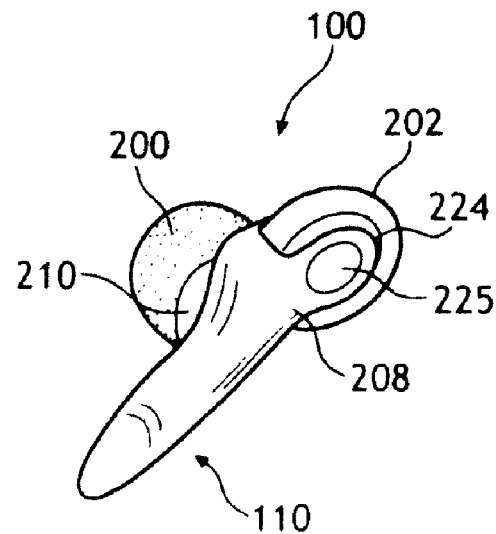
FIG. 21 is side perspective view of the eighth embodiment of a hearing protector of the present invention.

In FIG. 21, a further embodiment of the hearing protector 100 is depicted. This embodiment is almost identical to the embodiment described with respect to FIGS. 17-20 except the bow member is omitted. Specifically, there is no shoulder 106 or arm 108. Whilst the bow member may provide a measure of security against loss of the hearing protector 100 during wear, the advantage provided by omitting the bow member is that there is nothing over the user's ear (near junction 170, FIG. 2) that would interfere with the wearing of eye glasses. Handle 110 provides a grip for positioning and removing hearing protector 100 from the ear. All other previously described variations including but not limited to the use of unitary pads 200/202 or handle overlay 119 shall apply to this embodiment.

Figure 22:
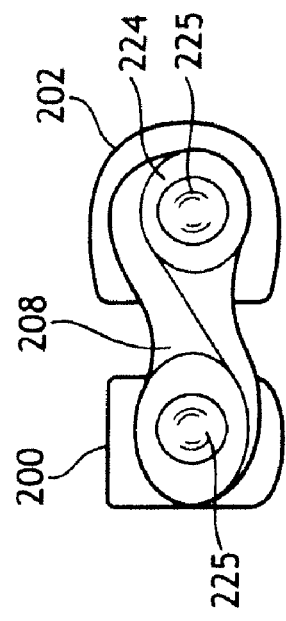
FIG. 22 is a side elevation view of the ninth embodiment of a hearing protector of the present invention.
Figure 23:
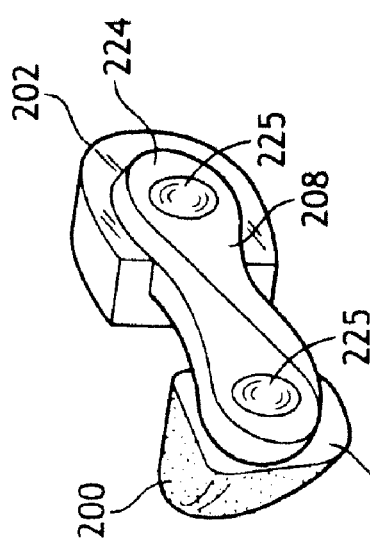
FIG. 23 is a front perspective view of the hearing protector of FIG. 22.

In FIGS. 22-23, still another embodiment of the hearing protector 100 is depicted. This embodiment is almost identical to the embodiment described with respect to FIG. 21 except the handle 110 is omitted. The advantage of this hearing protector is that it may be more comfortable for some than other hearing protectors that significantly enter the ear canal 26 (e.g. a foam ear plug that is compressed prior to insertion into the ear canal, and allowed to expand so that it stays in place). All other previously described variations including but not limited to the use of unitary pads 200/202 shall apply to this embodiment.

Figure 25:
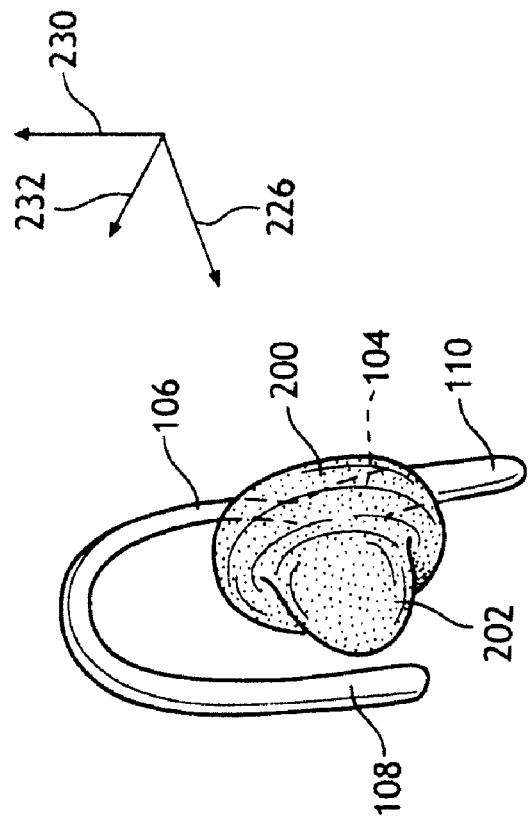
FIG. 25 is a front perspective view of the hearing protector of FIG. 24.
Figure 24:
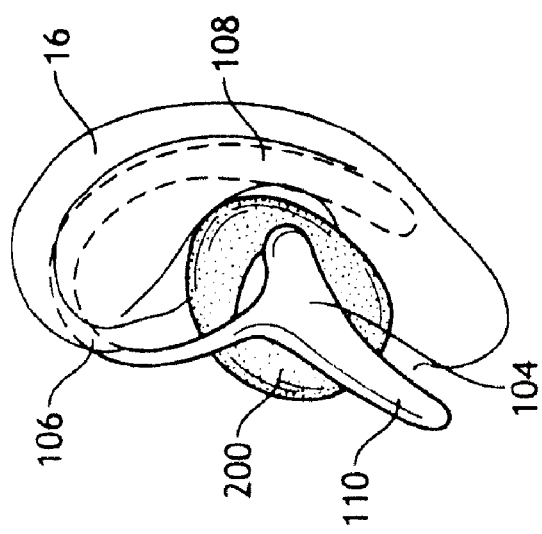
FIG. 24 is a side perspective view of the tenth embodiment of a hearing protector of the present invention.

Finally, in FIGS. 24-25, another embodiment of the hearing protector 100 is depicted. This embodiment is similar to the embodiment described with respect to FIGS. 22-23 except the pressure plate is enlarged and it may include additional sound attenuation for the EAM pad 200 and the pressure pad 202, such as has been described previously. In addition, the pressure pad 202 and EAM pad 200 are unitary in construction, and possibly integrally connected. In this particular embodiment, the pressure pad 202 attaches to the neck 104, and the EAM pad 202 is attached to the pressure pad 202. By outward appearance, the pressure pad is sandwiched between the EAM pad 200 and the neck 104. However, internally, the neck 104 may have flange extending therefrom that would provide stiffening for pressure pad 202 (similar to flange 222 at FIG. 20), and/or the neck may include a stem or the like extending into the EAM pad 200 (similar to that shown in FIGS. 6-8). The entire EAM pad 200/pressure pad 202 assembly may be selectively attachable by ball and socket, hook-and-loop, and magnet connections, or the like, as described previously.

The configuration shown in FIGS. 24-25 provides the advantages of a muff-style hearing protector without a head band or other attachment about the pinna. Further, it may be easier to remove and replace than some muff-style designs. As shown in FIGS. 24 and 25, the pressure plate is enlarged enough to fill or almost fill the area defined by the concha 24 and the anti-helix 18. Because human anatomy is varied from individual to individual, the dimensions of the pressure plate 208 in the y-direction 232 and z-direction 230 may be such that it fits most adults. It is contemplated that a variety of sizes may be offered. With respect to FIGS. 17-20, it is contemplated that in yet another embodiment, the pressure plate 208 may be configured as shown and described for the hearing protector of FIG. 24.

Referring now to FIGS. 6-7, 9-12, and 17-20, it is further contemplated that the arm member 108 may be shortened or even removed for easier placement onto the ear. With respect to FIGS. 17-20, it is contemplated that the pressure plate 208 may be configured as is shown in FIGS. 24-25. It is further contemplated that the embodiments shown in FIGS. 13-20 may have the EAM pad 200 replaced by an ear plug design such as those shown in FIGS. 3-4.

Although only a few exemplary embodiments of this invention have been described in detail above, those skilled in the art will readily appreciate that many modifications are possible in the exemplary embodiments without materially departing from the novel teachings and advantages of this invention. For example, any of the embodiments of the present invention may be adapted for use as an ear phone (not shown). As one skilled in the art of ear phone technology will realize, electronics for transmitting sound may be embedded in the ear clip and attached to speaker located in the neck 104. The plug member 102/EAM pad 200 may at least partially cover the speaker.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

The invention claimed is:

1. A hearing protection device for the passive attenuation of a single human ear canal, the device comprising:
   a shoulder, wherein a neck and a pressure plate extends therefrom, the neck having a stem protruding therefrom;
   a plug member covering the stem, wherein the plug member is configured to seal the human ear canal; and
   a pressure pad connected to a pressure plate;
   wherein the pressure pad and the plug member comprise an elastomeric material.

2. The hearing protection device of claim 1 wherein at least a partial arm is attached to the shoulder to form a bow member.

3. The hearing protection device of claim 2 wherein the bow member comprises a torsion spring.

4. The hearing protection device of claim 1 wherein the plug member is selectively attached to the neck member by a connector selected from the group consisting of a ball and socket, a hook and loop, a magnet, and an adhesive.

5. The hearing protection device of claim 1 wherein the stem is flexible.

6. The hearing protection device of claim 1 wherein the pressure pad is integrally attached to the pressure plate.

7. The hearing protection device of claim 6 wherein the pressure pad comprises indicia located on an outer surface.

8. The hearing protection device of claim 1 wherein the elastomeric material comprises foam.

9. The hearing protection device of claim 1 wherein the pressure pad and the plug member comprise identical types of material.

10. The hearing protection device of claim 1 further comprising a handle extending from the shoulder, neck, or pressure plate.

11. The hearing protection device of claim 10 wherein the handle comprises a touch indicia selected from the group consisting of: an overlay, detent, elastomeric material, and texture.

12. The hearing protection device of claim 1 wherein the pressure pad and the plug member are integrally connected.

13. The hearing protection device of claim 1 wherein the plug member is comprised of foam.

14. The hearing protection device of claim 1 wherein the pressure pad member and the plug member are located on opposite sides of the support structure.

15. The hearing protection device of claim 1 further comprising electronics for transmitting sound to the human ear canal, the electronics located in the neck.

16. A hearing protection device for the passive attenuation of sound at a single human ear canal, the device comprising:
   a neck member;
   a partial bow member for fitting over the top of a human ear, the partial bow member extending from the neck member;
   a pressure plate extending from the neck member or the partial bow member;
   an elastomeric EAM pad for engaging and sealing the ear canal, the EAM pad at least partially covering the neck member; and
   an elastomeric pressure pad at least partially covering the pressure plate.

17. The hearing protection device of claim 16 wherein the pressure pad is adapted to substantially fill an area defined by a user's concha and anti-helix to form a muff-style hearing protection device.

18. The hearing protection device of claim 16 wherein the pressure pad and the EAM pad are located on a common side of the partial bow member.

19. A method of providing hearing protection for a human ear comprising the steps of:
   occluding an ear canal with a plug member, wherein the plug member is attached to a neck having a stem protruding therefrom, and wherein neck is attached to a shoulder;
   placing a pressure pad between the ear canal and an anti-tragus region of the human ear to provide a force directed toward the plug member, wherein the pressure pad is connected to a pressure plate, and the pressure plate is connected to the neck or shoulder; and
   wherein the pressure pad and the plug member each comprise an elastomeric material.

\* \* \* \* \*